United States Patent
Müller et al.

(10) Patent No.: US 6,511,583 B1
(45) Date of Patent: Jan. 28, 2003

(54) METHOD FOR SEPARATING A LIQUID CRUDE ALDEHYDE MIXTURE BY DISTILLATION

(75) Inventors: Rolf Müller, Dannstadt-Schauernheim (DE); Willi Schönmann, Limburgerhof (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 196 days.

(21) Appl. No.: 09/937,311
(22) PCT Filed: Oct. 5, 2000
(86) PCT No.: PCT/EP00/02721
§ 371 (c)(1), (2), (4) Date: Sep. 24, 2001
(87) PCT Pub. No.: WO00/58255
PCT Pub. Date: Oct. 5, 2000

(30) Foreign Application Priority Data

Mar. 29, 1999 (DE) .......................... 199 14 259

(51) Int. Cl.⁷ .......................... B01D 3/14; C07C 45/82
(52) U.S. Cl. .................. 203/78; 203/99; 203/DIG. 19; 568/492
(58) Field of Search .................. 203/99, DIG. 19, 203/73, 78, 80, 100; 568/492, 449

(56) References Cited

U.S. PATENT DOCUMENTS

| | | | |
|---|---|---|---|
| 4,054,555 A | * 10/1977 | Ackermann et al. | 568/492 |
| 4,479,012 A | * 10/1984 | Fischer et al. | 203/87 |
| 4,684,750 A | 8/1987 | Kessen et al. | 568/883 |
| 4,950,800 A | * 8/1990 | Weber et al. | 568/492 |
| 5,064,508 A | * 11/1991 | Weber et al. | 203/38 |
| 5,102,505 A | 4/1992 | Sorensen | 203/91 |
| 5,227,544 A | 7/1993 | Thurman et al. | 568/881 |

FOREIGN PATENT DOCUMENTS

DE 33 20 648 12/1984

* cited by examiner

Primary Examiner—Virginia Manoharan
(74) Attorney, Agent, or Firm—Keil & Weinkauf

(57) ABSTRACT

In a process for the fractional distillation of a liquid crude aldehyde mixture including straight-chain and branched aldehydes, the product mixture is fractionated in a first distillation column to give a product stream of branched aldehyde, a product stream of straight-chain aldehyde and a further product stream including straight-chain aldehyde and the high boiling constituents. The further product stream is then fractionated in a second distillation column whose packing volume is a factor of from 50 to 200 smaller than that of the first distillation column to give a product stream of straight-chain aldehyde and a high boiler product stream.

8 Claims, 1 Drawing Sheet

METHOD FOR SEPARATING A LIQUID CRUDE ALDEHYDE MIXTURE BY DISTILLATION

The present invention relates to a process for the fractional distillation of a liquid crude aldehyde mixture which comprises essentially from 95 to 99.9% by weight, based on the total weight of the product mixture, of a straight-chain and a branched aldehyde.

Aldehydes are produced industrially by hydroformylation of olefins in the presence of cobalt or rhodium catalysts. Although straight-chain aldehydes are generally sought, the products obtained are, depending on the hydroformylation conditions, mixtures of straight-chain and branched aldehydes. In addition to the aldehydes, high-boiling aldehyde condensation products such as dimers, trimers and tetramers of the aldehydes and also the corresponding alcohols formed by reduction of the aldehydes are obtained as by-products in the hydroformylation.

The reaction mixture obtained in the hydroformylation therefore has to be fractionated. This is usually achieved by means of a two-stage distillation process using two separate distillation columns having approximately equal dimensions. In the first column, all the aldehyde is separated from the high-boiling constituents. The mixture of straight-chain and branched aldehyde is then fractionated in the second column.

The process using two separate columns is very energy intensive and costly in terms of materials and leads to a significant loss of aldehyde, since the high temperatures necessary for complete recovery of the high-boiling aldehyde promote the formation of high-boiling by-products.

The process described in EP 484 977 A seeks to avoid these disadvantages. In this process, only one distillation column is used for the fractionation of the crude aldehyde mixture and the distillation conditions are selected so that the branched aldehydes are taken off in liquid form in the upper region of the distillation column and the straight-chain aldehyde is separated into two product streams. The first product stream, which consists essentially of pure, straight-chain aldehyde, is taken off in vapor form in the lower region of the distillation column. The amount of this aldehyde product stream is not more than 70% by weight of the total amount of straight-chain aldehyde in the crude aldehyde mixture. The second product stream of straight-chain aldehyde is taken off as bottoms; it contains the major part of the high-boiling constituents. Although the process makes it possible to separate off the branched aldehydes, the straight-chain aldehydes are merely separated into two fractions of different purity, with the amount of the first relatively pure fraction making up at most 70% of the product used so that the amount of high-boiling constituents in the second fraction does not become excessively high. The amount of pure straight-chain aldehyde which can be achieved in practice using this process is thus only a maximum of 70% by weight of the straight-chain aldehyde present in the crude product mixture.

It is an object of the present invention to provide a process for fractionating a liquid crude aldehyde mixture which is less costly and allows the straight-chain aldehyde and the branched aldehyde to be obtained virtually completely in pure form.

We have found that this object is achieved by, in the fractionation of the crude aldehyde mixture in a first distillation column, taking off the branched aldehyde at or near the top of the distillation column, taking off the straight-chain aldehyde as a side stream in the lower region of the column and taking off a further product stream comprising the residual straight-chain aldehyde and the high-boiling constituents as bottoms, and fractionating the latter in a second, smaller distillation column.

The present invention accordingly provides a process for the fractional distillation of a crude aldehyde mixture comprising essentially from 94 to 99.8% by weight, based on the total weight of the crude aldehyde mixture, of a straight-chain and one or more branched aldehydes (the straight-chain and branched alcohols have the same number of carbon atoms), which process comprises A) feeding the crude aldehyde mixture into the middle region of a first distillation column having a plurality of theoretical plates and fractionating it in the column into
   i) a first aldehyde product stream which is taken off at or near the top of the distillation column and comprises essentially pure branched aldehyde,
   ii) a second aldehyde product stream which is taken off immediately above the vaporizer or further up in the region of the first 20% of the total theoretical plates and comprises essentially pure straight-chain aldehyde, and
   iii) a further product stream which comprises the high-boiling constituents and from 75 to 93% by weight, based on the total weight of the further product stream, of straight-chain aldehydes, and B) taking off the further product stream at the bottom of the first distillation column and passing it to a second distillation column whose packing volume is a factor of from 50 to 200 smaller than that of the first distillation column, and, in this second distillation column, fractionating it into a product stream which comprises essentially pure straight-chain aldehyde and is taken off at the top or near the top of the second distillation column and a product stream which comprises essentially the high-boiling constituents.

FIG. 1 schematically shows the process of the present invention.

The crude aldehyde mixture used can be any product mixture obtained from a hydroformylation process. Hydroformylation is a known process which is described, for example, in the U.S. Pat. Nos. 4,148,830; 4,247,486; 4,593,127 and in EP 404 193 and EP 484 977 A.

Starting materials used for the hydroformylation are, in particular, olefins having three or four carbon atoms, e.g. propylene, 1-butene, 2-butene (cis or trans) and isobutylene. The crude aldehyde mixture to be fractionated according to the present invention therefore preferably comprises straight-chain and branched $C_4$- or $C_5$-aldehydes.

The catalysts used for the hydroformylation are likewise known; they are described, for example, in the patent publications cited in EP 484 977 A.

The crude aldehyde mixture obtained in the hydroformylation comprises, apart from low-boiling constituents such as carbon monoxide and hydrogen, branched aldehydes, straight-chain aldehydes and higher-boiling constituents. The latter are by-products formed by condensation of the aldehydes to give dimers, trimers and tetramers and by reduction of the resulting aldehydes by hydrogen to form the corresponding alcohols. Aldehydes present in the crude aldehyde mixture can be, in particular, the $C_4$-aldehydes obtained by hydroformylation of propylene, e.g. n-butyraldehyde and isobutyraldehyde, or the $C_5$-aldehydes obtained by hydroformylation of butene, e.g. n-valeraldehyde and the branched $C_5$-aldehydes 2-methylbutyraldehyde, 3-methylbutyraldehyde and pivaldehyde. The composition of the crude aldehyde mixture is dependent on the conditions in the hydroformylation process; the weight ratio of the straight-chain aldehyde and the branched aldehyde(s) is generally in the range from about 8:2 to about 99:1. The total amount of aldehydes in the crude aldehyde mixture is generally from 94 to 99.8% by weight, preferably from 97 to 99.8% by weight. The remainder is made up by the abovementioned lighter-boiling and especially the higher-boiling constituents, namely about 0.1–3% by weight of condensation products and about 0.1–3% by weight of alcohols.

The process of the present invention can be carried out in any suitable distillation column. Suitable columns are, for example, tray columns, e.g. valve tray columns, and preferably packed columns. The packing can be customary random beds of packing elements or be ordered packing, with preference being given to the latter. Particular preference is given to using Mellapak® from Sulzer (ordered packing).

The number of theoretical plates has to be large enough for the desired fractionation to be effected. It is generally in the range from about 40 to 100 theoretical plates.

The first distillation column is equipped with the necessary means for operation, e.g. vaporizer, condenser, instrumentation, connections for introducing and taking off products, etc. The crude aldehyde mixture is generally fed continuously into the middle region (about the middle third) of the distillation column, based on the number of theoretical plates. The exact point at which the mixture is fed in is not critical and can be determined by a person skilled in the art using standard methods.

The distillation conditions in the first distillation column are selected so that separation into the product streams described below is achieved. The temperature at the bottom is generally about 1–40° C., preferably about 10–30° C., above the boiling point of the straight-chain aldehyde. The pressure at the top of the column is generally in the range from 1.0 bar to 1.5 bar (absolute).

Under these circumstances, the mixture is separated in the first distillation column into the following three product streams:

i) A first aldehyde product stream which is taken off at the top or near the top of the distillation column as a liquid side stream. It consists essentially of pure branched aldehyde. The branched aldehydes distilled off via the top are condensed in a customary manner, with part of the condensate being able to be returned to the column as runback. The reflux ratio is generally in the range from 20 to 30. The pure branched aldehyde then leaves the plant. If constituents which are even more volatile than the branched aldehydes are present in the crude aldehyde mixture, for example carbon monoxide, hydrogen, olefins and paraffins, these are likewise taken off at the top and discharged.

ii) A second aldehyde product stream which is taken off immediately above the vaporizer or further up in the region of the first 20% of the total theoretical plates. The second aldehyde product stream is preferably taken off in the region of the first 10% of the total number of theoretical plates, in particular below the first theoretical plate, i.e. immediately above the bottom. The aldehyde product stream is particularly preferably taken off in vapor form.

The second aldehyde product stream consists essentially of pure straight-chain aldehyde. In general, more than 70% by weight, preferably more than 80% by weight, in particular more than 90% by weight, of the total straight-chain aldehyde present in the crude aldehyde mixture is taken off.

iii) A further, high-boiling product stream which is taken off in liquid form at the bottom of the column. This product stream comprises the abovementioned high-boiling constituents and from 75 to 93% by weight, preferably from 80 to 93% by weight, in particular from 85 to 93% by weight and particularly preferably from 88 to 92% by weight, based on the total weight of the further high-boiling product stream, of straight-chain aldehyde. The amount of straight-chain aldehyde is generally about 2 to 5% by weight of the total amount of straight-chain aldehyde.

The further high-boiling product stream iii) is then fed into the middle region (about the middle third of the theoretical plates) of a second distillation column. This is smaller than the first distillation column. The difference can be expressed in terms of the packing volume, i.e. the packing volume of the second column is a factor of from 50 to 200, preferably from 80 to 180, in particular from 100 to 170 and particularly preferably from 120 to 160, smaller than the packing volume of the first column.

The ratio of the diameter of the first column to that of the second column is in the range from 10:1 to 4:1.

The column is equipped with the means necessary for operation, e.g. vaporizer, condenser, instrumentation, connections for introducing and taking off the products, etc.

The distillation conditions are selected so that fractionation into a product stream comprising essentially pure straight-chain aldehyde and a product stream comprising the high boilers is obtained. The temperature at the bottom is generally about 1–40° C., preferably about 10–30° C., above the boiling point of the straight-chain aldehyde. The pressure at the top of the column is generally in the range from 1.0 bar to 1.5 bar (absolute). The pure straight-chain aldehyde is taken off at the top or near the top of the distillation column, preferably in liquid form, and is particularly preferably fed back into the first distillation column above the point at which the product stream ii) is taken off. It is preferably fed in at about the same height as the point at which the crude aldehyde mixture is fed in, e.g. by mixing into the crude aldehyde feed stream. In this preferred embodiment, essentially all of the straight-chain aldehyde present in the crude aldehyde mixture is obtained as product stream ii). The product stream comprising the high boilers is taken off at the bottom of the second distillation column and leaves the plant.

The process of the present invention has the advantage that it can be carried out at lower cost and under gentle conditions and essentially all the straight-chain and branched aldehydes are obtained in pure form. Both the straight-chain aldehydes and the branched aldehydes are obtained in a purity of from 99 to 99.98% by weight. In general, the high boiler content of the straight-chain aldehydes is less than 0.5% by weight, in particular less than 0.2% by weight.

BRIEF DESCRIPTION OF THE DRAWING

The following examples illustrate the invention with reference to the FIGURE, without restricting the scope of the invention.

EXAMPLE 1

Figure 1:
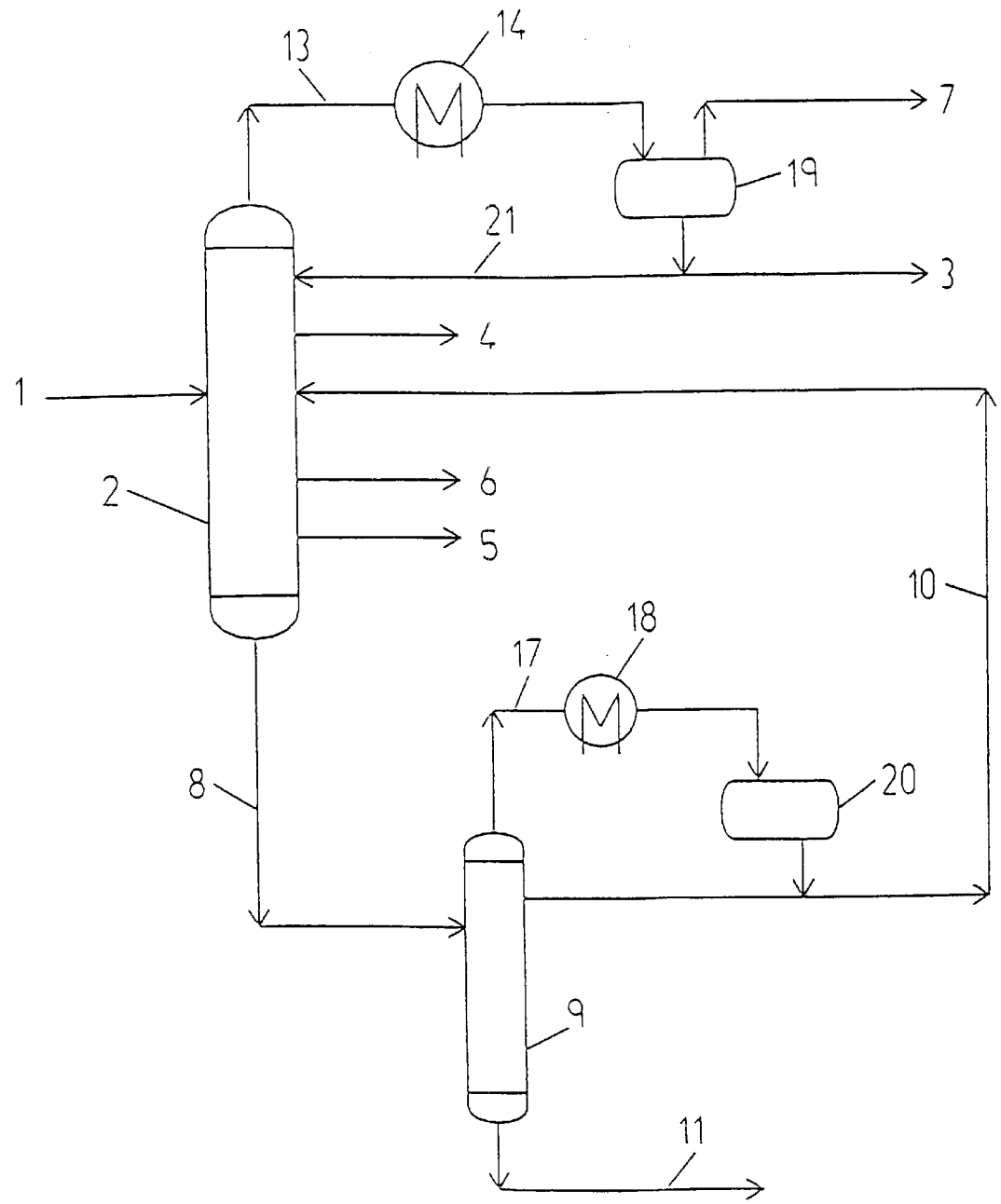

The starting material used was a crude aldehyde mixture from hydroformylation comprising isobutyraldehyde and n-butyraldehyde and containing 0.01% by weight of constituents having a lower boiling point than isobutyraldehyde and 0.5% by weight of constituents having a higher boiling point than n-butyraldehyde. As first distillation column, use was made of a column 2 having 80 theoretical plates and packed with Mellapak® from Sulzer (ordered packing). The crude aldehyde mixture was introduced as feed stream 1 having a mass flow of 10,000 kg/h at the 43rd theoretical plate of the column 2. The distillation was carried out at a temperature at the bottom of 87° C. and an absolute pressure at the top of 1.24 bar. Isobutyraldehyde and low boilers were taken off at the top as stream 13. The isobutyraldehyde was condensed in the condenser 14 and collected in the vessel 19. The volatile, noncondensible constituents were discharged from the plant at stream 7. Part of the condensate collected in the vessel 19 was returned as runback stream 21 to the top region of the column 2 (reflux ratio 22). Pure isobutyraldehyde was discharged from the plant as stream 3 in an amount of about 1400 kg/h.

Pure n-butyraldehyde was taken off as a gaseous side stream 5 in an amount of about 8600 kg/h below the first theoretical plate of the column 2. The high-boiling product stream 8 was taken off as a bottom stream of about 600 kg/h and passed to the second distillation column 9 which was also packed with Mellapak® from Sulzer. Its packing volume was a factor of about 140 smaller than that of the first distillation column (diameter ratio of large to small column about 8). The distillation in the second column was carried out at a temperature at the bottom of 134° C. and an absolute pressure at the top of 1.2 bar. In this way, the stream 8 was distilled to give about 550 kg/h of n-butyraldehyde which was taken off as stream 10 near the top of the column 9 and returned to the 43rd theoretical plate of column 2. Alternatively, the n-butyraldehyde can be taken off at the top as stream 17, condensed in the condenser 18 and collected in the vessel 20 and, if desired, returned to the column 2. The bottoms of column 9 were discharged from the plant as stream 11 in an amount of about 50 kg/h.

The purity of the isobutyraldehyde obtained was 99.9% by weight and the purity of the n-butyraldehyde was 99.75% by weight. 99.9% of the aldehydes present in the feed stream 1 were recovered as pure components.

EXAMPLE 2

The following example of a computer simulation serves to illustrate the invention further, likewise with reference to the figure. A crude aldehyde mixture of isobutyraldehyde and n-butyraldehyde containing 0.01% by weight of constituents having a boiling point lower than that of isobutyraldehyde and about 1.3% by weight of constituents having a boiling point higher than that of n-butyraldehyde is introduced as feed stream 1 having a mass flow of 9500 kg/h at the 58th theoretical plate of the column 2 (same column as in Example 1). The distillation is carried out at a temperature at the bottom of the column 2 of 98° C. and an absolute pressure at the top of 1.2 bar. Isobutyraldehyde and the low boilers are taken off at the top as stream 13 and condensed in the condenser 14 except for the gaseous constituents which leave the plant as stream 7 (1 kg/h). Part of the condensate collected in the vessel 19 is returned as runback 21 to the column 2 (reflux ratio 30), while pure isobutyraldehyde (about 1400 kg/h) is discharged as stream 3. A gaseous side stream 6 of about 7974 kg/h of pure n-butyraldehyde was taken off below the 10th theoretical plate of the column 2. The liquid bottoms 8 of about 600 kg/h are fed into the middle region of the column 9 (same column as in Example 1). The distillation in the column 9 is carried out at a temperature at the bottom of 134° C. and a pressure at the top of 1.2 bar (absolute). 475 kg/h of n-butyraldehyde are taken off as stream 10 in the upper region of the column and returned to the middle region of the column 2. The bottoms 11 from the column 9 (about 125 kg/h) comprise the higher-boiling constituents and leave the plant. The purity of the n-butyraldehyde and isobutyraldehyde obtained is in each case 99.9% by weight.

EXAMPLE 3

The following computer simulation, too, serves to illustrate the invention further, with reference to the figure.

A crude aldehyde mixture of isovaleraldehyde and n-valeraldehyde containing 0.2% by weight of constituents having a boiling point lower than that of isovaleraldehyde and about 0.6% by weight of constituents having a boiling point higher than that of n-valeraldehyde is introduced at a mass flow of 11,000 kg/h as feed stream 1 at the 58th theoretical plate of the column (same column as in Example 1). The distillation is carried out at a temperature at the bottom of the column of 120° C. and an absolute pressure at the top of 1.2 bar. Isovaleraldehyde and low boilers are taken off at the top as stream 13 and condensed in the condenser 14 except for the gaseous constituents which leave the plant as stream 7 (1 kg/h). Part of the condensate collected in the vessel 19 is returned as runback 21 (reflux ratio 30) to the column 2, while pure isovaleraldehyde (about 1650 kg/h) leaves the plant as stream 3. Pure n-valeraldehyde is taken off as a gaseous side stream 6 in an amount of about 9279 kg/h below the 10th theoretical plate of the column 2. The liquid bottoms 8 of about 600 kg/h are introduced into the middle region of the column 9 (same column as in Example 1). The distillation in the column 9 is carried out at a temperature at the bottom of 170° C. and a pressure at the top of 1.2 bar (absolute). The bottoms 11 from this column (about 70 kg/h) comprise the higher-boiling constituents which leave the plant. About 530 kg/h of n-valeraldehyde are taken off as stream 10 at the top of the column 9 and are returned to the middle region of the column 2. The purity of the n-valeraldehyde and isovaleraldehyde obtained is in each case 99.9% by weight.

We claim:
1. A process for the fractional distillation of a crude aldehyde mixture comprising essentially from 94 to 99.8% by weight of aldehydes, based on the total weight of the crude aldehyde mixture, wherein the crude aldehyde mixture contains straight-chain and at least one branched aldehyde, which comprises
   A) feeding the crude aldehyde mixture into the middle region of a first distillation column having a plurality of theoretical plates and fractionating it in the column into
     i) a first aldehyde product stream which is taken off at the top of the distillation column and consists essentially of purified at least one branched aldehyde,
     ii) a second aldehyde product stream which is taken off immediately above a vaporizer or further up in a region of the first 20% of the total theoretical plates and consists essentially of purified straight-chain aldehyde, and
     iii) a third product stream which comprises high-boiling constituents and from 75 to 93% by weight, based on the total weight of the third product stream, of straight-chain aldehydes, and
   B) passing the third product stream to a second distillation column whose packing volume is a factor of from 50 to 200 smaller than that of the first distillation column, and, in this second distillation column, fractionating said third product stream into an aldehyde product stream which comprises essentially further purified straight-chain aldehyde and is taken off at the top of the second distillation column and a product stream which comprises the constituents having a boiling point higher than that of the straight-chain aldehyde.

2. A process as claimed in claim 1, wherein the second aldehyde product stream ii) is taken off in vapor form.

3. A process as claimed in claim 1, wherein the second aldehyde product stream ii) is taken off in the region of the first 10% of the total theoretical plates of the first distillation column.

4. A process as claimed in claim 1, wherein more than 70% by weight of the total straight-chain aldehyde present in the crude aldehyde mixture is obtained as product stream ii).

5. A process as claimed in claim 4, wherein more than 90% by weight of the total straight-chain aldehyde present in the crude aldehyde mixture is obtained as product stream ii).

6. A process as claimed in claim 1, wherein the third product stream iii) contains from 75 to 92% by weight of straight-chain aldehyde.

7. A process as claimed in claim 1, wherein the aldehyde product stream obtained in the second distillation column is returned to the first distillation column.

8. A process as claimed in claim 1, wherein the crude aldehyde mixture comprises straight-chain and branched $C_4$- or $C_5$-aldehydes.

* * * * *

UNITED STATES PATENT AND TRADEMARK OFFICE
CERTIFICATE OF CORRECTION

PATENT NO.    : 6,511,583 B1
DATED         : January 28, 2003
INVENTOR(S)   : Mueller et al.

It is certified that error appears in the above-identified patent and that said Letters Patent is hereby corrected as shown below:

<u>Title page,</u>
Item [22], PCT Filed, "Oct. 5, 2000" should be -- Mar. 28, 2000 --.

Signed and Sealed this

Eighteenth Day of March, 2003

JAMES E. ROGAN
*Director of the United States Patent and Trademark Office*